(12) United States Patent
Bokrantz

(10) Patent No.: US 12,053,647 B2
(45) Date of Patent: Aug. 6, 2024

(54) SYSTEM AND METHOD FOR RADIOTHERAPY TREATMENT PLANNING

(71) Applicant: RaySearch Laboratories AB, Stockholm (SE)

(72) Inventor: Rasmus Bokrantz, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 920 days.

(21) Appl. No.: 17/056,477

(22) PCT Filed: May 24, 2019

(86) PCT No.: PCT/EP2019/063523
§ 371 (c)(1),
(2) Date: Nov. 18, 2020

(87) PCT Pub. No.: WO2019/228932
PCT Pub. Date: Dec. 5, 2019

(65) Prior Publication Data
US 2021/0244969 A1      Aug. 12, 2021

(30) Foreign Application Priority Data
May 30, 2018   (EP) .................... 18175106

(51) Int. Cl.
*A61N 5/10*           (2006.01)

(52) U.S. Cl.
CPC ......... *A61N 5/1036* (2013.01); *A61N 5/1047* (2013.01)

(58) Field of Classification Search
None
See application file for complete search history.

(56) References Cited

U.S. PATENT DOCUMENTS

| 2004/0190680 | A1 | 9/2004 | Chang |
| 2006/0045238 | A1* | 3/2006 | Nguyen ................ A61N 5/103 378/65 |
| 2006/0256915 | A1* | 11/2006 | Otto ..................... A61N 5/1031 378/65 |
| 2010/0219356 | A1 | 9/2010 | Bzdusek |
| 2017/0354832 | A1* | 12/2017 | Bush ..................... A61N 5/103 |
| 2020/0139156 | A1* | 5/2020 | Sheng ................... G16H 30/40 |

OTHER PUBLICATIONS

P. Zhang, Ph.D. et al., "Optimization of Collimator Trajectory in Volumetric Modulated Arc Therapy: Development and Evaluation for Paraspinal SBRT," Int. J. Radiation Oncology Biol. Phys., 2010, vol. 77, No. 2, pp. 591-599.

* cited by examiner

*Primary Examiner* — Thaddeus B Cox
(74) *Attorney, Agent, or Firm* — Faegre Drinker Biddle & Reath LLP

(57) ABSTRACT

Automatic radiation therapy treatment planning for generating a plan to be delivered from at least one beam angle, using a collimator having a variable collimator angle. Delivery times are determined for a number of possible collimator angles, and the optimization problem is defined to take the delivery times into account when selecting the collimator angles to be used when delivering the radiation.

14 Claims, 6 Drawing Sheets

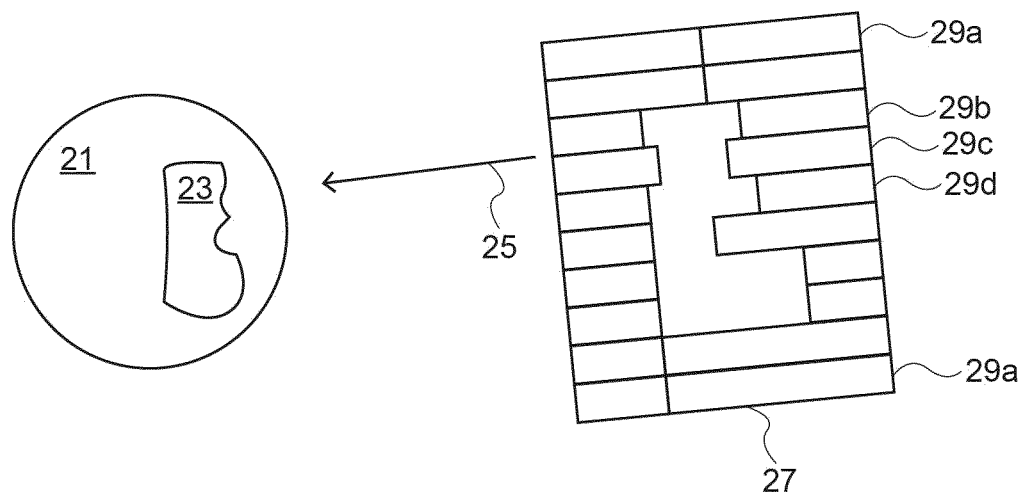
FIGURE 2
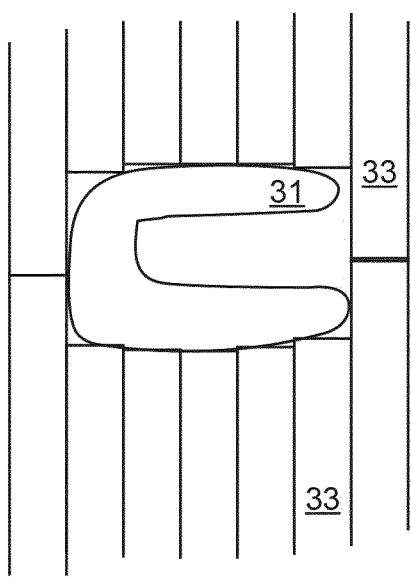
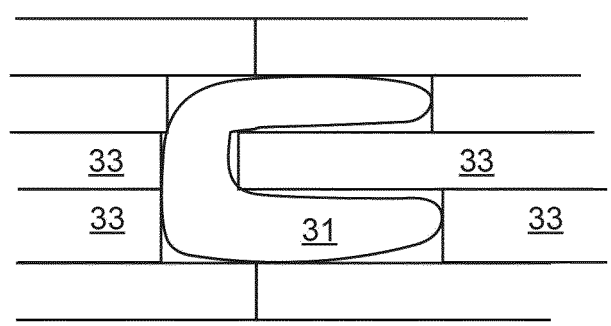
FIGURE 3a          FIGURE 3b

SYSTEM AND METHOD FOR RADIOTHERAPY TREATMENT PLANNING

This application is the National Stage of International Application No. PCT/EP2019/063523, filed May 24, 2019, and claims benefit of European Patent Application No. 18175106.6, filed May 30, 2018, the entire contents of which are incorporated by reference herein.

TECHNICAL FIELD

The present invention relates to a system and a method for radiation therapy treatment planning, in particular for intensity-modulated radiation therapy treatment planning.

BACKGROUND

The invention relates to radiation therapy treatment in which beams of photons are sent towards a treatment area of a patient to treat that area. It is important to shape the beam in such a way that the area to be treated receives the desired dose while limiting the dose to surrounding tissue. In particular, sensitive organs, known as organs at risk, should be protected as much as possible. To achieve this, a gantry that can rotate around the patient is often used to provide the radiation in beams from different angles, in such a way that all beams will reach the target while each part of the surrounding tissue will receive dose from only one or a few beams. The gantry may be able to rotate fully around the patient, or rotate partially along a fraction of the circumference. The gantry may provide radiation in a continuous arc as it moves around the patient, or stop to deliver static beams at certain angles. A treatment fraction may be composed of multiples arcs or static beams, or a combination thereof. The patient couch may also rotate during arc delivery or between the delivery of static beams, in order to modify the direction of irradiation relative to the patient. There are other means for varying the beam direction, for example, the radiation source may be mounted on a movable robotic arm, but for the purpose of this discussion the gantry is used as an illustrative example. Typically, in photon therapy, a collimator placed in the beam plane, that is, perpendicular to the beam central axis, is used to shape the beam in order for the deposited dose to match the prescribed dose a precisely as possible.

A multi-leaf collimator (MLC) comprises a frame having a rectangular opening and a number of pairs of leaves placed adjacent each other along opposing sides of the opening. The two leaves in a leaf pair are placed opposite each other and can move in such a way that they can either close a part of the opening completely or expose all or a portion of that part of the opening. Each leaf pair defines a linear portion of the MLC. Various techniques exist for calculating movement patterns for the MLC during the beam delivery. For example, in sliding window delivery, the leaves move unidirectionally across the field, with the distances between opposing leaves selected in such a way that radiation will be let through in areas that should be exposed to radiation, for an amount of time determined by a fluence map, while being blocked from other areas. Multiple sliding window leaf sweeps can be delivered in sequence without switching off the irradiation, producing a movement pattern where the leaves move back and forth over the treated region.

The MLC may be rotated to different angles around the beam central axis, to limit the beam in the most suitable way given the patient geometry. A given rotation of the MLC relative to the beam central axis is called a collimator angle. It may also be feasible to rotate the MLC to different collimator angles at different gantry angles, as the patient geometry will change depending on the beam direction. The MLC may also be rotated during the delivery of a static beam, i.e., the collimator angle may be a function of the delivery time or the cumulative monitor units (MUs) of the beam. In today's conventional practice, the collimator angle is selected manually and kept constant over the whole arc or static beam.

Treatment with a dynamic collimator angle is particularly useful for treating targets having a complex geometry or for avoiding organs at risk that are in the beam path at certain beam directions. For continuous arc delivery, this involves determining a trajectory for the collimator angle as a function of the direction of irradiation, and the delivery time or cumulative MU.

It has been proposed to adapt the collimator angle in dependence of the patient anatomy. For example, Zhang et al.: Optimization of collimator trajectory in volumetric modulated arc therapy: development and evaluation for paraspinal SBRT, Int. J. Radiation Oncology Biol. Phys., Vol. 77, No. 2, pp. 591-599, 2010, proposes a collimator trajectory optimization in which the collimator angle is always determined in dependence of the spinal cord in such a way that the direction of the movement of the leaves is parallel to the principal direction of the spinal cord. This enables optimal protection of the spinal cord from radiation.

Based on the same type of consideration, Yang et al.: Choreographing couch and collimator in volumetric modulated arc therapy, Int. J. Radiation Oncology Biol. Phys., Vol. 80, No. 4, pp. 1238-1247, 2011, proposes a collimator trajectory optimization in which the collimator angle is always determined in such a way that the direction of the movement of the leaves is parallel to the principal direction of the overlap between a target and an organ at risk.

Hence, both the two articles cited above are focused on orienting the collimator so that the leaves may block out organs at risk as completely as possible MacDonald et al.: Dynamic collimator trajectory algorithm for multiple metastases dynamic conformal arc treatment planning, Med. Phys. 45(1), January 2018, discloses an algorithm based on determining the amount of non-target area that is open to exposure from the radiation beam for each possible collimator angle and minimizing this exposed non-target tissue.

Determining the collimator angle based on patient geometry may be useful in certain specific situations, such as the ones handled by Yang et al., Zhang et al., and MacDonald et al. above. Such reasoning cannot be applied in the general case, however. Patient geometry does not always enable the identification of a particularly suitable collimator angle.

SUMMARY

It is an object of the present invention to enable the optimization of a collimator angle trajectory in radiation treatment planning.

The invention relates to a treatment planning method for generating a treatment plan for radiation therapy in which a collimator is used to shape the radiation beam, where the radiation is planned to be delivered from at least one beam direction.

said method comprising the steps of
    obtaining a first fluence map for the or each of the at least one beam direction,
    for each first fluence map, determining a first and a second value of a delivery parameter for the fluence map for a first and a second possible collimator angle, respectively, the delivery parameter being based on delivery time or monitor units for the fluence map for the respective combination of beam direction and collimator angle, obtaining an optimization problem comprising an objective function that depends on the delivery parameter, performing an optimization with respect to the optimization problem, said optimization comprising selecting at least one of the possible collimator angles for each beam direction, on the basis of the first and second values of the delivery parameter, an output from the optimization being a collimator angle trajectory, and using the result of the optimization to generate a treatment plan that will follow the collimator angle trajectory.

The first three steps may be performed in any suitable order. The delivery parameter may be based on the delivery time for the fluence map using the respective collimator angle and the optimization comprises selecting collimator angles in such a way as to minimize the delivery time. Alternatively, or in addition, the delivery parameter may be based on the MU for the fluence map using the respective collimator angle and the optimization comprises selecting collimator angles in such a way as to minimize the MU.

Because the delivery time and number of MUs are directly additive quantities, the selection of collimator angles based on minimization of these quantities has the advantage that it allows the collimator angle to be selected separately for each fluence map, thus enabling a division of the optimization problem into a number of separate, simpler problems which may be added to produce the final result. In addition to the delivery time and/or monitor units, any time needed to rotate the collimator between different fluence maps should be considered in the optimization, but the algorithm will still only involve linear addition of time contributions.

The method is particularly well suited for treatment plan optimization in which fluence is considered, but may also be used for other treatment planning methods. The angle trajectory may be composed of a single point if an optimal static collimator angle should be selected.

The optimization is performed in such a way as to optimize a value based on the parameter values for all selected collimator angles. In the simplest case this may involve optimizing the sum, or a weighted sum of parameter values for all selected collimator angles.

The step of using the result of the optimization to generate a treatment plan typically comprises the step of mapping fluence maps for the selected collimator angles to control points. In a preferred embodiment, the step of using the result of the optimization to generate a treatment plan also comprises the step of converting the collimator angle trajectory to a smooth function to make the collimator movements smoother.

All collimator angles to be considered for a particular beam direction may be determined at once, and the corresponding delivery parameter values may be determined subsequently. Alternatively, a first set one or more tentative collimator angles and their corresponding delivery parameters may be determined first, and then one or more second tentative collimator angles may be selected and their respective delivery parameter values determined. The second tentative collimator angle or angles may be selected based on the tentative values and delivery parameters for the first set. This may be repeated as many times as desired, in an iterative process to select the best possible collimator angles for each beam direction, to be used in the optimization.

One or more collimator angles may be used for dose delivery for each beam direction. If more than one collimator angle may be used for each beam direction, the method further comprises obtaining a second fluence map for each of the beam directions, determining a first and second value of the delivery parameter for the first and second possible collimator angle for the second fluence maps, respectively, and optimizing the objective function in dependence of the delivery parameter values for the first and second fluence maps for each of the beam directions.

In a preferred embodiment, the optimization problem comprises constraints that limit at least one of the magnitude and the speed of the collimator rotations. Typically, this means that the objective function depends on at least one of the magnitude and the speed of the collimator rotations, but the magnitude and/or speed may alternatively be included in the form of constraints.

In a preferred embodiment, the optimization problem is formulated as a graph problem with respect to a graph with nodes corresponding to the at least first and second collimator angle of each fluence map of each beam angle, and edges corresponding to rotations between collimator angles. Known methods for solving the graph problem include shortest path algorithms, minimum cost flow algorithms, and linear programming algorithms.

The plan obtained by the inventive method may be intended for delivery in a system arranged to irradiate during movement of the beam, or for delivery in a system arranged to keep the beam static during irradiation.

Preferably the rotation of the collimator is also restrained by imposing a penalty on the magnitude of the rotation of the collimator between the first and the second beam angle. This will ensure that collimator rotation that only provides a negligible benefit in objective function value is avoided, thereby ensuring that the optimized treatment plan is not unnecessarily geometrically complex.

The invention also relates to a computer program product comprising computer readable code means which, when executed in a computer, will cause the computer to perform the method as described above. The invention also relates to a non-transitory computer readable medium encoded with computer executable instructions which, when run in a first computer device will cause the device to perform the method as described above. The invention also relates to a computer system comprising a processor, a data memory and a program memory, wherein the program memory comprises a computer program product or a non-transitory computer readable medium as defined above.

Tests have shown that the delivery time for a plan optimized using the inventive method can be reduced considerably compared to a plan having a fixed optimized collimator angle. Even larger time savings may be possible compared to manually selected fixed collimator angles that are sub-optimal with respect to delivery time. Short delivery times have several advantages, such as reduction of discomfort for the patient, a reduced risk for geometric errors due to intrafraction motion, and potentially reduced scatter and leakage irradiation. Furthermore, there often exists a tradeoff between delivery time and plan quality in treatment planning for radiation therapy. The time-saving provided by dynamic collimator rotation may therefore also have a positive impact on treatment plan quality.

The suggested method is more generally applicable than the prior art methods outlined above, in that it may be used for any body part and any tumor configuration. The method is primarily useful if a sliding window leaf motion pattern is used for the MLC. The method can however, be applied to any type of external beam delivery that uses an MLC to modulate fluence.

The method according to the invention could be incorporated in any fluence-based radiation treatment planning system as an alternative to manually defined collimator angle trajectories.

BRIEF DESCRIPTION OF THE DRAWINGS

The invention will be described in more detail in the following, by way of example and with reference to the appended drawings, in which

FIG. 2 schematically shows the relationship between a beam, a collimator and a target.

FIGS. 3a and 3b illustrate the effect of different collimator angles for the same target.

DETAILED DESCRIPTION

Figure 1:
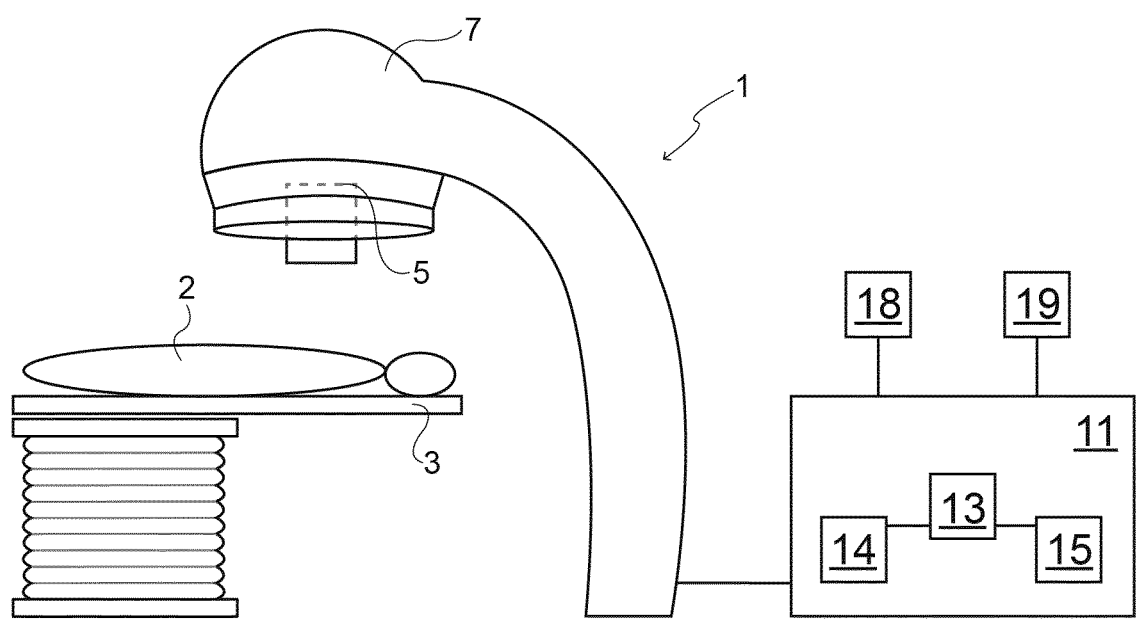
FIG. 1 shows a radiation therapy delivery system in which the method according to the invention may be implemented.

FIG. 1 is an overview of a system 1 for radiotherapy treatment imaging and/or planning. As will be understood, such systems may be designed in any suitable way and the design shown in FIG. 1 is only an example. A patient 2 is positioned on a treatment couch 3. The system comprises a radiation source 5 mounted in a gantry 7 for emitting radiation towards the patient positioned on the couch 3. Typically, the couch 3 and the gantry 7 are movable in several dimensions relative to each other, to enable radiation to be delivered to the patient as flexibly and correctly as possible. In particular, the gantry can rotate around the couch, either between certain angles or a full 360° around the whole couch. Such systems are well known to the skilled person. The gantry is either arranged to stop at certain gantry angles to emit radiation towards the patient, which will enter the patient at corresponding beam directions, or to emit radiation continuously while rotating. In the latter case, for the purpose of this invention, the arc described by the rotating gantry is discretized into arc sectors.

The system also comprises a computer 11 which may be used for radiotherapy treatment planning and/or for controlling radiotherapy treatment. As will be understood, the computer 11 may be a separate unit not connected to the imaging unit. The computer 11 comprises a processor 13, a data memory 14, and a program memory 15. Preferably, one or more user input means 18, 19 are also present, in the form of a keyboard, a mouse, a joystick, voice recognition means or any other available user input means. The user input means may also be arranged to receive data from an external memory unit.

The data memory 14 comprises clinical data and/or other information used to obtain a treatment plan. The data memory 14 also comprises one or more dose maps for one or more patients to be used in treatment planning according to embodiments of the invention. The program memory 15 holds a computer program, known per se, including the optimization problem and arranged for treatment plan optimization.

For the purpose of treatment planning, a separate computer system similar to the computer 11 but not connected to a treatment or imaging system may be used, basing its calculations on data provided from an external imaging system.

Optimization based on minimizing an objective function is well known in the art. In this case, the optimization problem includes an objective function based on limiting the delivery time or MUs as discussed above.

As will be understood, the data memory 14 and the program memory 15 are shown and discussed only schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

FIG. 2 shows schematically a patient 21 having a target, or a treatment volume 23 that is being irradiated from a particular beam angle indicated by an arrow 25. In the beam a collimator 27 is placed. The collimator comprises a number of leaf pairs 29a, 29b, . . . , 29f, each of which may be closed to block the beam, such as pair 29a, or to let the beam through, such as pairs 29b, 29c, 29d. The leaf pairs are controlled so that the opening in the collimator will expose an area designed to control the fluence to provide the best possible dose distribution to the patient. In a more complex situation there may be more than one treatment volume that should receive radiation and/or one or more organs at risk, that should be protected from radiation.

FIGS. 3a and 3b illustrate the effect of changing the collimator angle, using an example in which the beam's-eye-view projection of the treatment volume 31 is roughly U shaped. In FIG. 3a, the collimator leaves 33 move perpendicularly to the legs of the U, which as can be seen means that the tissue inside of the U shape 31 will be exposed to radiation. In FIG. 3b the collimator is rotated 90° compared to the situation shown in FIG. 3a. As can be seen, the collimator leaves 33 can be used to block the surrounding tissue both inside and around the U-shaped treatment volume 31. Similar situations may arise where there are multiple targets and/or organs at risk close to the target.

As the gantry moves around the patient, the outline of the target, and its position relative to any organ at risk, as seen by the beam, will change and the collimator angle should therefore be changed to adapt to the geometry for each gantry angle. Dynamic motion of the collimator may lead to improved dose distributions and shortened treatment delivery times. At the same time, adjusting the collimator angle for each gantry angle takes time, depending on the magnitude of the adjustment.

The constant adjustment of the collimator angles over the movement of the gantry around the patient, or the adjustment of the collimator angle as a function of the delivery time or cumulative number of MUs, constitutes a collimator angle trajectory which may be optimized in any suitable way, for example as a shortest path problem. The collimator trajectory is optimized taking into account the sum of the delivery times for all fluence maps and preferably also the time required for each adjustment of the collimator angle in-between fluence maps. The objective function of the collimator angle optimization may, furthermore, include other terms such as penalties on the magnitude or speed of the collimator angle adjustments. This means that it may not be feasible or optimal to select strictly the collimator angles associated with the shortest delivery times, if the time to adjust the collimator angle for each new gantry angle outweighs the time gained by using a particular collimator angle, or if the penalties on collimator rotation outweigh the time gained by a using a particular collimator angle. One could also include constraints in the collimator angle optimization to prevent too large or time-consuming rotations. The total objective function for the collimator angle optimization, which should be minimized, is the sum of the delivery times and other penalties across all fluence maps and, if applicable, the time required for each adjustment of the collimator angle between gantry angles.

For selection of a static collimator angle, the collimator angle trajectory reduces to a single point, and the time required to adjust of the collimator angle between gantry angles reduces to zero.

Figure 4:
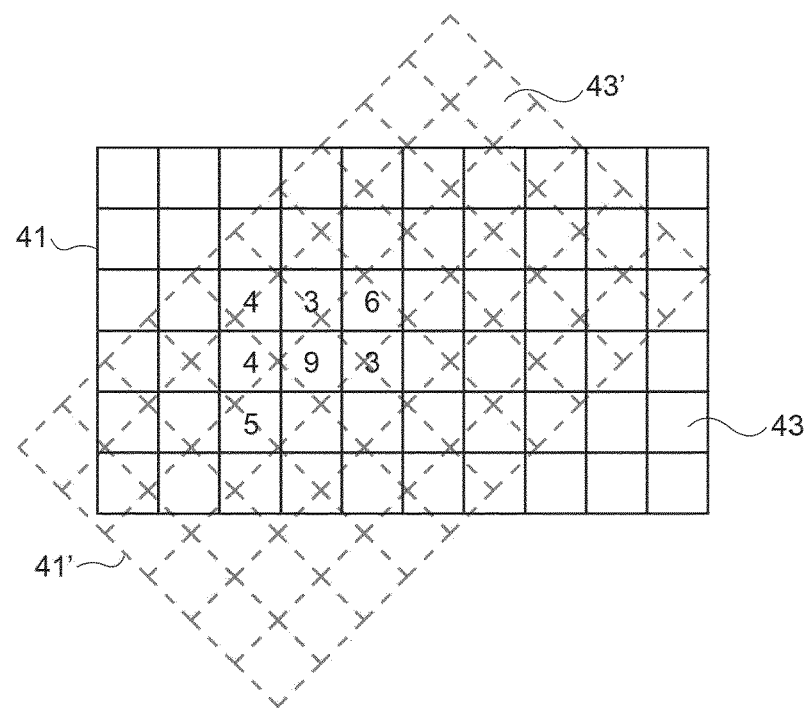
FIG. 4 illustrates the mapping of a fluence map onto different collimator angles.

For each gantry angle a fluence map is calculated, indicating the amount of radiation that should be applied to each portion of the treatment area. FIG. 4 shows the mapping of the fluence map onto a collimator 41 having a first orientation in the beam plane, seen as if the beam is directed towards the page. The fluence map is divided into sub-areas 43. As will be understood, if the collimator is rotated, as illustrated by the dashed lines indicating a different orientation 41' of the collimator, a new mapping of the fluence map onto the collimator must be determined, resulting in new sub-areas 43'. The updated mapping representing the rotated collimator may calculated by resampling the original fluence map onto a rotated grid using a suitable interpolation method, such as bilinear or nearest neighbor interpolation.

Figure 5:
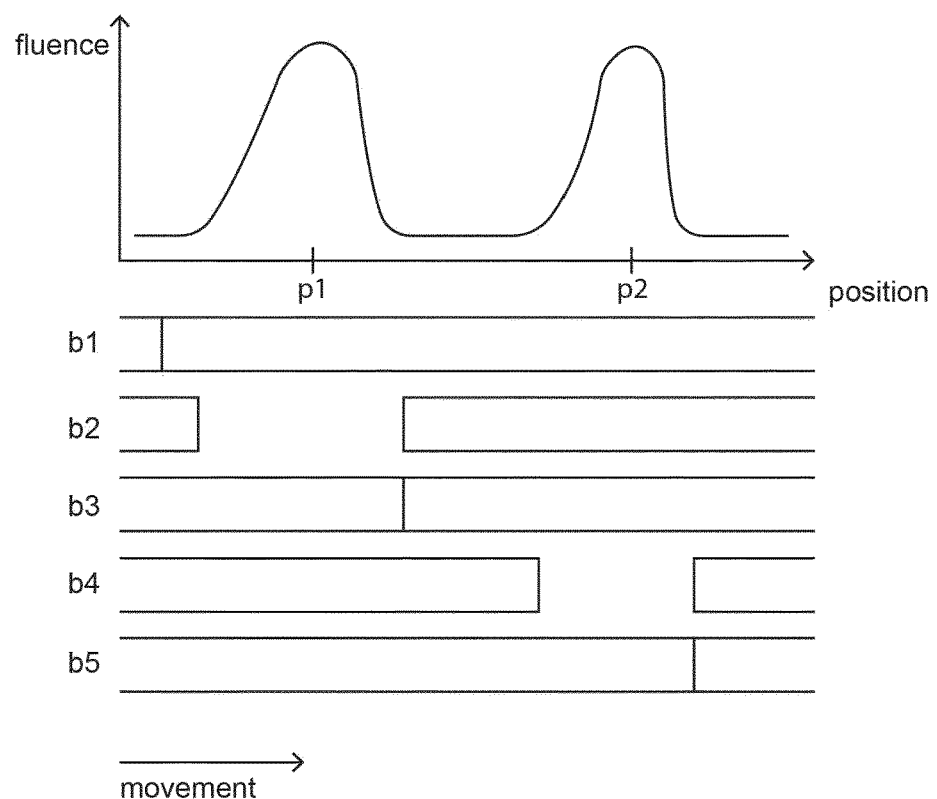
FIG. 5 illustrates leaf movement of the MLC.

FIG. 5 illustrates the movement of a pair of collimator leaves, in a sliding window type movement, in dependence of the fluence that should be applied in the area that may be covered or exposed by this leaf pair, which is a linear area. The upper part of FIG. 5, marked a, is a diagram of the fluence over the linear area. As can be seen, there are two peaks at a first p1 and a second position p2, respectively, corresponding to a first and a second area that should be exposed to high amounts of radiation. The remaining parts of the linear area in this example should not be exposed to radiation.

The lower part of FIG. 5 is a time sequence of leaf pair positions for one leaf pair, calculated by a sliding window algorithm, shown in relation to the fluence diagram. In a first position b1, the leaves are closed and in the far left position in the collimator opening. The leaves then move together from left to right as indicated by the arrow below the diagram. When the leftmost edge of the first peak is reached, the left leaf stops and the right leaf continues moving until the whole area corresponding to the first fluence peak is exposed as shown in b2. The exact movement pattern and the exposure time is determined by the desired fluence to the exposed area. After a certain time, the left leaf will follow the right leaf so that they will be closed at the right edge of the first peak as shown in b3 and continue moving together until they reach the leftmost edge of the second peak. Here the left leaf will stop and the right leaf will continue to move until the whole area corresponding to the second fluence peak is exposed as shown in b4. After a certain time, the left leaf will follow the right leaf so they will be closed at the right edge of the second peak as shown in b5, and will move together to the rightmost edge of the collimator opening. The next movement will be right to left as seen in the Figure, at the next gantry angle and typically at a different collimator angle.

Figure 6A:
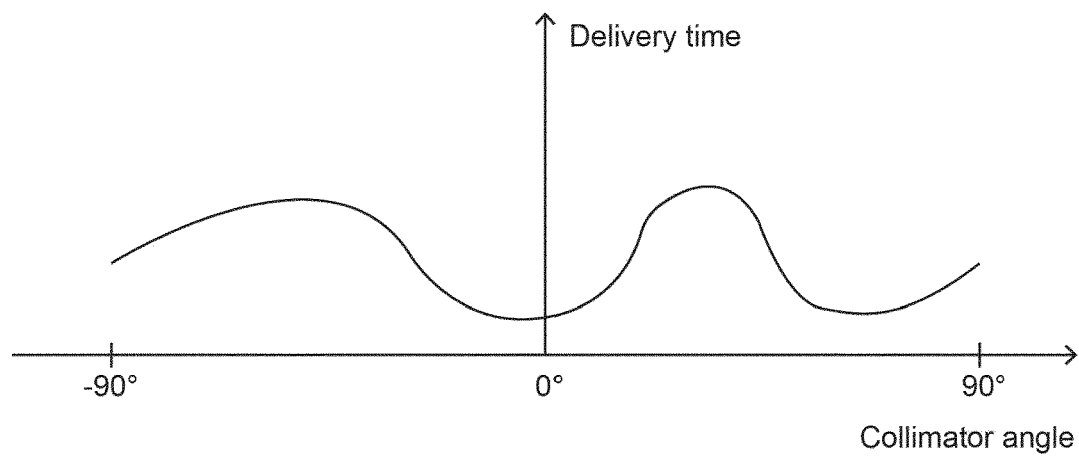
FIGS. 6a, 6b, and 6c show three different graphs depicting delivery times in dependence of collimator angle for different gantry angles.
Figure 6B:
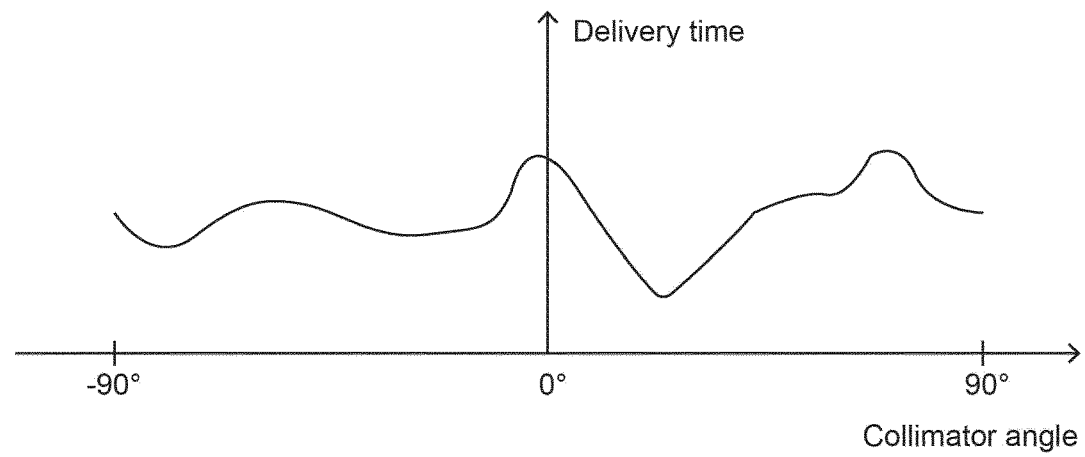
Figure 6C:
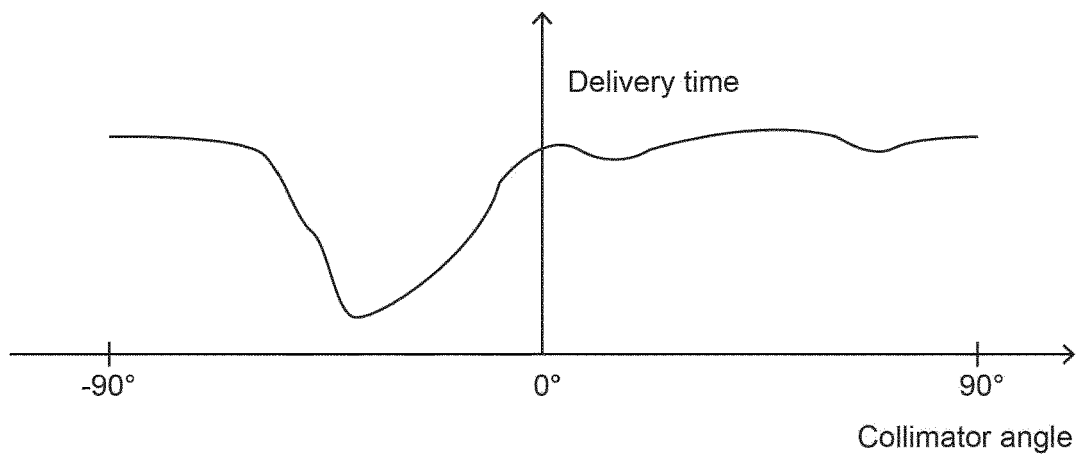

FIGS. 6a, 6b and 6c show three different diagrams each representing, for one gantry angle, the delivery times for each possible collimator angle. According to the invention the corresponding information is determined for a number of gantry angles, for example through 360 degrees at 10-degree intervals, that is, 36 diagrams.

In the first diagram, shown in FIG. 6a and corresponding to a gantry angle of 0°, the lowest value for the objective function is achieved at a collimator angle of approximately 60°. For technical reasons an angular area of 180°, ranging from −90° to 90° is applied. There is another near minimum at approximately 60°. In the second diagram, shown in FIG. 6b and corresponding to a gantry angle of approximately 40°, the shortest possible delivery time is achieved at a collimator angle of about 30°. In the third diagram, shown in FIG. 6c and corresponding to a gantry angle of 90°, the shortest possible delivery time is achieved at a collimator angle of about −40°. As will be understood, these are just arbitrary examples and a real set of curves could look very different. Also, it is not necessary according to the invention to determine or display the curves in any way.

Figure 7A:
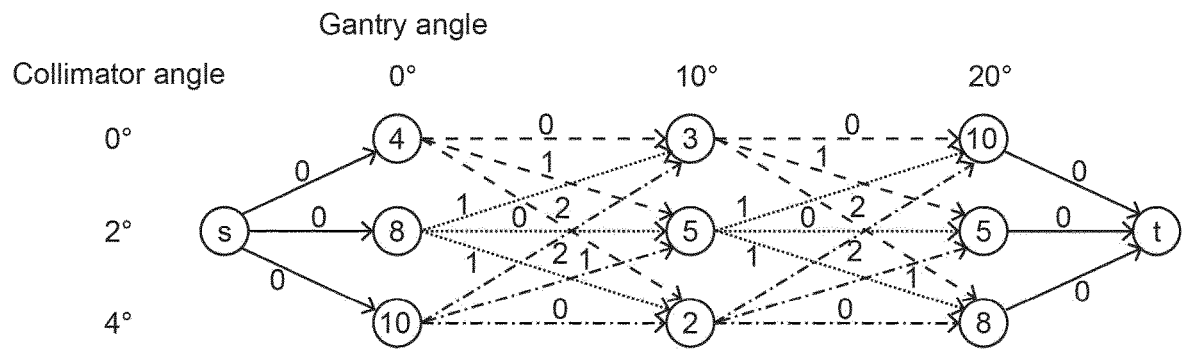
FIGS. 7a and 7b illustrate delivery times used as input data to the treatment planning in the form of a shortest path problem.
Figure 7B:
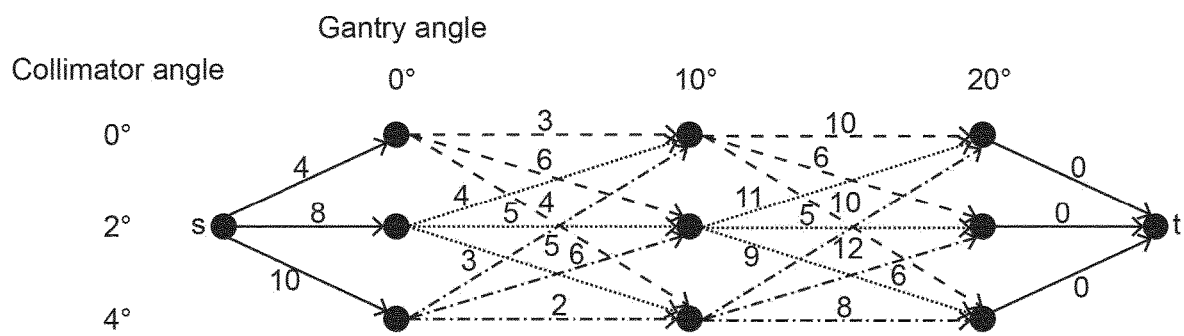

FIGS. 7a and 7b illustrate an example graph comprising, a source node s and a sink node t, and for each combination of beam direction and collimator angle between the source node and the sink node, a node listing the delivery time. In graph algorithms, the nodes may also be referred to as vertices. For each change from one beam direction to the next, the collimator angle can change freely in this example. Between each pair of nodes, directed edges are defined corresponding to the magnitude of the change in collimator angle. For visibility, different patterns are used for the edges starting from different nodes. The beam directions selected correspond to fluence maps. In a practical implementation, where the beam direction was changed by moving the gantry, as shown in FIG. 1, the graph would comprise one layer for each fluence map around the whole gantry trajectory, and each layer would have nodes with values for a number of possible collimator angles. The number of nodes in each layer may be limited by a maximum possible rotation of the collimator, or the nodes may be a discretization of all angles from 0° to 360°. FIGS. 7a and 7b only show three beam directions, from 0° to 20° and for each beam direction only 3 collimator angles, 0°, 2° and 4°. The values are chosen only as examples to illustrate the principle. In FIG. 7a each node displays the fluence delivery time as a number, and each edge is assigned a penalty related to the change in collimator angle. In this example, a penalty of 1 per 2 degrees of collimator rotation is assigned to the edges. This is shown in FIG. 7a by the number 0, 1 or 2, respectively, assigned to each of the edges. An edge between two nodes corresponding to the same collimator angle receives no penalty, hence the number 0. An edge between two nodes with a 2-degree difference receives a penalty of 1. An edge between two nodes with a 4-degree difference, from 0 to 4 degrees or vice versa, receives a penalty of 2. Of course, in a full-scale example, larger differences between collimator angles must also be considered, with larger penalties.

As may be seen in this example, the shortest possible delivery time for the fluence at a gantry angle of 0° is 4 seconds at a collimator angle of 0°. The shortest possible delivery time at a gantry angle of 10° is 2 seconds at a collimator angle of 4°. The shortest possible delivery time at a gantry angle of 20° is 5 seconds at a collimator angle of 2°.

Hence, if only the times for actually delivering the fluence for each gantry angle were considered, the collimator angle should follow a trajectory from 0° to 4° to 2°. However, the overall objective function value also depends on the penalties assigned to the edges. Therefore, in some cases it better to select, for one or both gantry angles, collimator angles for which the delivery time will be slightly longer but that will reduce the overall objective function value by limiting the contribution due to penalties for adjusting the collimator angle. In a typical case, however, the delivery time for the collimator rotation is included in the delivery time for the corresponding fluence map. In this case, there is already a penalty on collimator rotation. It may still be feasible, even in such cases, to add a penalty on the rotation of the collimator, to keep the angular trajectory of the collimator from becoming unnecessarily complex.

FIG. 7b shows the same situation as in FIG. 7a, reformulated to a standard directed acyclic graph by transferring the node weights to the incident edges. As can be seen, each edge is assigned a number that is the sum of the penalty related to the change in collimator angle represented by that edge and the fluence delivery time of the next node obtained from FIG. 7a. For example, for a gantry angle of 10° and a collimator angle of 0°, the edges from the nodes representing collimator angles 0°, 2° and 4° at a beam direction of 10° are assigned 3+0=3, 5+1=6 and 3+2=5, respectively. Similarly, for a gantry angle of 20° and a collimator angle of 2°, the edges from the nodes representing collimator angles 0°, 2° and 4° at a gantry angle of 0° are assigned 5+1=6, 5+0=5 and 5+1=6, respectively.

Generally, the optimization problem should involve a limiting function designed to reduce the magnitude of angular movement of the collimator between two gantry angles. The limiting function may be designed as a constraint, strictly limiting the movement to a maximum angular difference. The limiting function may also be designed as a penalty to add an amount of time to the calculated total delivery time, in dependence of the angular movement the collimator undergoes between two gantry angles. For example, the penalty could allow free movement up to n degrees and add a fixed time for each degree exceeding n, n being any number between 0 and 360. Of course, a combination of the two may also be applied, that is, both a strict limitation of the angular movement and a penalty set to restrict the magnitude of the movement.

Figure 8:
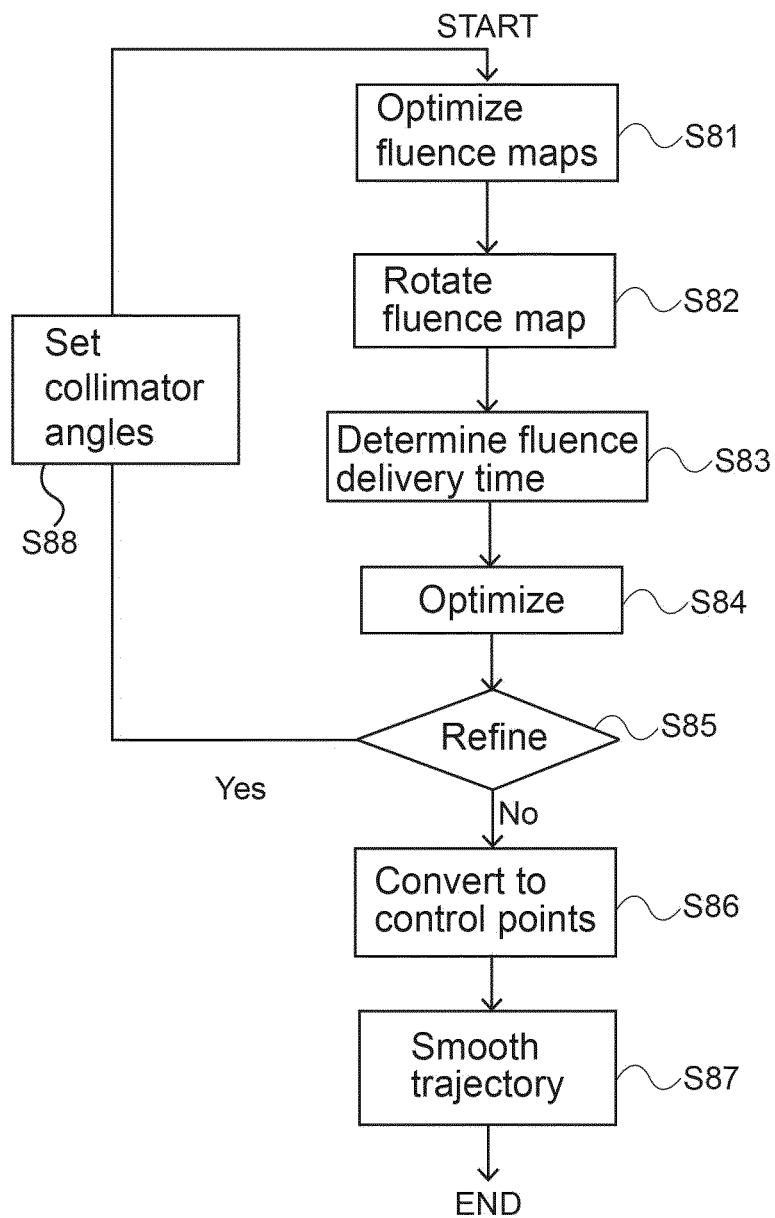
FIG. 8 is an overall flowchart of an embodiment of the inventive method.

FIG. 8 is a flowchart of an embodiment of the inventive method. The outcome of this flowchart may be used as an optimized treatment plan or may be used as a starting point for further optimization.

Before or during the first step, the arc described by the gantry movement is discretized into a number of arc sectors, for example, each covering 10°. This discretization into sectors is useful if the gantry movement is continuous during radiation. In other delivery systems the gantry moves between predefined angles and stands still which the radiation is delivered. In this latter case, the angles in which the gantry delivers radiation should be identified in or before the first step S81. A discretization of the collimator angles into steps to be considered is also performed before or as part of the second step S82. Before step S84 an objective function is defined or obtained in some other way, minimizing delivery times and or number of monitor units.

In the first step S81, fluence map optimization is performed for each sector, or gantry angle, as the case may be. The fluence map optimization is performed for a static beam although in the typical case the beam will not be static. The discretization of arc sectors may be different than the discretization of fluence maps. For example, more than one fluence map may be used to represent an arc sector.

In a second step S82 the optimized fluence map for each gantry angle is rotated onto possible orientations of the collimator, as previously discretized, and the rotated fluence map is resampled onto the original fluence profile for each collimator angle. As illustrated in FIG. 4, this involves interpolation, for example, linear interpolation.

In a third step S83, the delivery time required to deliver each of the fluence map determined in step S82 is determined. As mentioned above and discussed in connection with FIG. 5, the delivery times may be calculated with respect to sliding window leaf motion, or by another type of collimator leaf movement. The time required for sliding window delivery of a fluence map may be calculated by determining the minimum time required for delivery of the linear portion of the fluence map corresponding to each leaf pair and then taking the maximum of these numbers. The minimum time necessary to reproduce a one-dimensional fluence profile associated with a single leaf pair can, given some preselected start and end positions for each of the leaves, be calculated as the time for movement of the leaves from the start to the end positions at the maximum leaf speed plus the time that the leaves need to be in static positions to modulate the fluence, as described in conjunction with FIG. 5. The leaves need to be in static positions for a number of monitor units given by the sum positive gradients of the fluence profile, i.e. $MU = x_1 + \Sigma_{i=2,\ldots,n} \max(x_i - x_{i-1}, 0)$ where x is a vector of discretized fluence values at consecutive positions. A number of monitor units is directly proportional to a time duration if the dose rate (the number of MUs per time unit) of the treatment machine is constant.

In steps S82 and S83 an iterative procedure may be applied, in which one or more tentative collimator angles are selected and the delivery time is determined for each of these tentative collimator angles. In dependence of these delivery times, the tentative collimator angles and their respective delivery times may be used in the subsequent optimization, or new tentative collimator angles may be selected and the fluence maps rotated onto the new set of tentative collimator angles. The selection of new tentative collimator angles is preferably made in dependence of the delivery times for the first tentative collimator angles, for example, close to the first tentative collimator angle that yields the best delivery time. Alternatively, a number of collimator angles may be selected at once and used, together with their determined delivery times, in the subsequent optimization.

In a fourth step S84, the collimator angle trajectory minimizing the objective function is calculated, preferably subject to constraints on the maximum collimator rotation speed. In this example, minimizing the objective function is equivalent to minimizing the overall delivery time. This can be achieved by solving a shortest path problem from a source node to a sink node over a layered directed graph where the layers correspond to the fluence maps and the nodes of each layer correspond to the discrete collimator angles. Alternatively, a minimum cost flow algorithm or linear programming algorithm may be applied. Shortest path, minimum cost flow and linear programming algorithms are all known to the skilled person. The graph has edges from all nodes of a layer to all nodes of the next layer as illustrated in FIGS. 7a and 7b. The length of each edge is the delivery time, or Monitor Unit, associated with the node that the edge originates from, plus a penalty term that is proportional to the angular difference between the two nodes that the edge connects. Edges that connect pairs of nodes with a larger angular difference than what can be realized by collimator rotation at the maximum speed are given infinite length.

In a fifth step S86 the fluence maps for the selected collimator angles are converted to control points. If the collimator is a sliding window type collimator, this involves using a sliding window sequencer that takes the coupling between adjacent fluence maps into account. The result of this calculation is a sequence of control points where the collimator angles are kept constant within each arc sector and rotates to the next collimator angle at the transition from one arc sector to the next.

In a sixth step S87 the collimator angle trajectory is converted to a smooth function representing a trajectory that is feasible with respect to the maximum collimator rotation speed. This smoothing can be implemented by any suitable method, for example, by a least square fit to the original constant angles mentioned for step S86, subject to linear constraints that prevent violations of the maximum collimator rotation speed.

The selection of collimator angles may be refined by repeating steps S81-S84 a suitable number of times with the fluence maps of step S81 rotated according to the selection of collimator angles determined in step S84. This is shown in FIG. 8 as a decision step S85 between steps S84 and S86. If it is decided that the plan should be refined, the collimator angles determined in step S84 are set to be used in the next iteration and the process reverts to step S81. If not, the procedure continues with step S86, as described above.

The outcome of step S87 is a set of control points, which may be used as they are or may be further optimized using direct machine parameter optimization. The control points define the leaf positions for the MLC and configuration of other beam limiting devices that may be present, such as jaws. Each control point also specifies the number of monitor units to be delivered until the next control point. The exact format of the control points varies with the type of delivery machine.

The invention claimed is:

1. A treatment planning method for generating a treatment plan for radiation therapy in which a collimator is used to shape a radiation beam, where radiation is planned to be delivered from at least one beam direction, said method comprising:
   obtaining, by a processor, a first fluence map for each beam direction;
   for each first fluence map, determining, by the processor, a first and a second value of a delivery parameter for the fluence map for a first and a second possible collimator angle, respectively, the delivery parameter being based on delivery time or monitor units for the fluence map for the respective combination of beam direction and collimator angle;
   obtaining, by the processor, an optimization problem comprising an objective function that depends on the delivery parameter;
   performing, by the processor, an optimization with respect to the optimization problem, said optimization comprising selecting at least one of the possible collimator angles for each beam direction, on the basis of the first and second values of the delivery parameter, an output from the optimization being a collimator angle trajectory; and
   using, by the processor, a result of the optimization to generate a treatment plan that will follow the collimator angle trajectory, and communicating, by the processor, the generated treatment plan to a radiation therapy system for performing the radiation therapy.

2. The treatment planning method according to claim 1, wherein the delivery parameter is based on the delivery time for the fluence map using a respective collimator angle and the optimization comprises selecting collimator angles in such a way as to minimize the delivery time.

3. The treatment planning method according to claim 1, wherein the delivery parameter is based on the number of monitor units for the fluence map using a respective collimator angle and the optimization comprises selecting collimator angles in such a way as to minimize the number of monitor units.

4. The treatment planning method according to claim 1, wherein the optimization is performed in such a way as to optimize a sum of parameter values for all selected collimator angles.

5. The treatment planning method according to claim 1, wherein the step of using the result of the optimization to generate a treatment plan comprises the step of converting fluence maps for the selected collimator angles to control points.

6. The treatment planning method according to claim 5, wherein the step of using the result of the optimization to generate a treatment plan further comprises the step of converting the collimator angle trajectory to a smooth function.

7. The treatment planning method according to claim 1, wherein the step of determining a first and a second value of a delivery parameter for the fluence map for a first and a second possible collimator angle, respectively, includes selecting at least a first tentative collimator angle, determining a tentative value of the delivery parameter for each of the at least first tentative collimator angle, selecting at least one second tentative collimator angle based on the tentative values for the at least first tentative collimator angle and determining a tentative value of the delivery parameter for each of the at least second tentative collimator angles.

8. The treatment planning method according to claim 1, further comprising obtaining a second fluence map for each beam direction, determining a first and second value of the delivery parameter for the first and second possible collimator angle, respectively, for the second fluence maps and optimizing the objective function in dependence of the delivery parameter values for the first and second fluence maps for each of the beam directions.

9. The method according to claim 1, wherein the optimization problem comprises constraints that limit at least one of a magnitude and a speed of collimator rotations, and wherein the objective function depends on at least one of the magnitude and the speed of the collimator rotations.

10. The method according to claim 1, wherein the optimization problem is formulated as a graph problem with respect to a graph with nodes corresponding to at least first and second collimator angles of each fluence map of a beam angle, and edges corresponding to rotations between collimator angles.

11. The method according to claim 1, wherein the selection is also based on a time required for rotating the collimator by imposing a penalty on a magnitude of the rotation of the collimator between a first and a second beam angle.

12. A computer program product comprising non-transitory computer readable code means which, when executed in a computer, will cause the computer to perform the method according to claim 1.

13. A computer system comprising a processor, a data memory and a program memory, wherein the program memory comprises the computer program product according to claim 12.

14. A non-transitory computer readable medium encoded with computer executable instructions which, when run in a first computer device will cause the device to perform the method according to claim 1.

* * * * *